United States Patent
Gounder et al.

(10) Patent No.: US 11,292,806 B2
(45) Date of Patent: Apr. 5, 2022

(54) PROCESSES FOR PREPARING SORBOSE FROM GLUCOSE

(71) Applicant: Purdue Research Foundation, West Lafayette, IN (US)

(72) Inventors: Rajamani Gounder, West Lafayette, IN (US); Michael Jonathan Cordon, West Lafayette, IN (US); Alyssa M. LaRue, West Lafayette, IN (US); Zige Huang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 262 days.

(21) Appl. No.: 16/787,402

(22) Filed: Feb. 11, 2020

(65) Prior Publication Data
US 2020/0255467 A1 Aug. 13, 2020

Related U.S. Application Data

(60) Provisional application No. 62/803,719, filed on Feb. 11, 2019.

(51) Int. Cl.
*C07H 3/02* (2006.01)
*C07H 1/00* (2006.01)
*B01J 29/89* (2006.01)

(52) U.S. Cl.
CPC ............... *C07H 3/02* (2013.01); *B01J 29/89* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 9,255,120 B2* | 2/2016 | Davis | C07H 3/02 |
| 2017/0129913 A1* | 5/2017 | Shunmugavel | C01B 37/005 |

OTHER PUBLICATIONS

Cordon et al., Angew. Chem. Int. Ed. 2020, 59, 19102-19102. (Year: 2020).*
Angyal, Stephen J., "The Lobry de Bruyn-Alberda van Ekenstein Transformation and Related Reactions", Topics in Current Chemistry, vol. 215, Springer-Verlag Berlin Heidelberg 2001, (14 pages).
Bermejo-Deval, R. et al., "Metalloenzyme-Like Catalyzed Isomerizations of Sugars by Lewis Acid Zeolites", PNAS, vol. 109, No. 25, 2012, (pp. 9727-9732).
Bermejo-Deval, R. et al., "Active Sites in Sn-Beta for Glucose Isomerization to Fructose and Epimerization to Mannose", ACS Catal. 4, 2014, (pp. 2288-2297).
Bermejo-Deval, R. et al., "Framework and Extraframework Tin Sites in Zeolite Beta React Glucose Differently", ACS Catal. 2, 2012, (pp. 2705-2713).
Cordon M.J. et al., "Deactivation of Sn-Beta Zeolites Caused by Structural Transformation of Hydrophobic to Hydrophilic Micropores During Aqueous-Phase Glucose Isomerization", Catal. Sci. Technol. 9, 2019, (pp. 1654-1668).
Cordon, M.J. et al., "Dominant Role of Entropy in Stabilizing Sugar Isomerization Transition States within Hydrophobic Zeolite Pores", J. Am. Chem. Soc. 140, 2018, (pp. 14244-14266).
Davis, M.E., "Heterogeneous Catalysis for the Conversion of Sugars into Polymers", Top. Catal 58, 2015, (pp. 405-409).
Dusselier, M. et al., "Shape-Selective Zeolite Catalysis for Bioplastics Production", sciencemag.org, vol. 349, Issue 6243, 2015 (pp. 78-81).
Gounder, R. et al., "Titanium-Beta Zeolites Catalyze the Stereospecific Isomerization of D-Glucose to L-Sorbose via Intramolecular C5-C1 Hydride Shift", ACS Catal. 3, 2013, (pp. 1469-1476).
Ikeue, K. et al., "Characterization of Ti-Beta Zeolites and Their Reactivity for the Photocatalytic Reduction of CO2 with H2O", J. Synchrotron Rad. 8, 2001, (pp. 602-604).
Roman-Leshkov et al., "Mechanism of Glucose Isomerization Using A Solid Lewis Acid Catalyst in Water", Angew. Chem. Int. Ed. 49, 2010, (pp. 8954-8957).

* cited by examiner

*Primary Examiner* — Traviss C McIntosh, III
(74) *Attorney, Agent, or Firm* — Hartman Global IP Law; Gary M. Hartman; Domenica N. S. Hartman

(57) ABSTRACT

Processes for converting glucose to sorbose with tailored selectivity. The processes include contacting glucose with a silica-containing structure that includes a zeolite having a topology of a 10-membered ring or smaller and Lewis acidic $M^{4+}$ framework centers, wherein M is Ti, Sn, Zr, or Hf. Contacting the glucose is conducted under reaction conditions sufficient to isomerize the glucose to sorbose.

17 Claims, 8 Drawing Sheets

Table 1. Site and structural characterization data for Lewis acidic zeolite and zeotype samples.

| Sample | $V_{ads}$ (N$_2$, 77 K) (cm$^3$ g$^{-1}$) | Si/M[a] | Nominal Pore Size (Å)[c] | Primary Micropore Ring Sizes[d] |
|---|---|---|---|---|
| Ti-Beta-F-282 | 0.20 | 282 | 0.70 | 12 |
| Ti-Beta-F-155 | 0.20 | 155 | 0.70 | 12 |
| Ti-Beta-F-133 | 0.21 | 133 | 0.70 | 12 |
| Ti-Beta-OH | 0.23 | 46 | 0.70 | 12 |
| Zr-Beta-F | | 170[b] | 0.70 | 12 |
| Hf-Beta-F | | 150[b] | 0.70 | 12 |
| Ti-MFI | | 305 | 0.55 | 10 |
| Ti-MFI-NS | 0.18 | | 0.55 | 10 |
| Ti-CON | | | 0.55-0.70 | 12, 10 |
| Ti-MCM-41 | | | >1.5 | >20 |
| Ti-CHA | | | 0.38 | 8 |

[a] Metal densities determined from AAS measurements unless otherwise noted.

[b] Metal densities determined from EDS measurements.

[c] Pore diameters of substantial size to allow glucose diffusion into microporous channels.

[d] Number of tetrahedral atoms that comprise the primary pore(s) of the given zeolite topology.

FIG. 5

Table 2. Reaction conditions, conversions, and selectivities at 373 K for M-Beta zeolites which reflect solution compositions studied during $^{13}$C NMR experiments.

| Sample | Catalyst/Solution Ratio[a] | Reaction Time (h) | $X_{fructose}$ | $X_{sorbose}$ | Selectivity[b] |
|---|---|---|---|---|---|
| Ti-Beta-F-282 | 50 | 3 | 6.0 | 3.9 | 0.7 |
| Ti-Beta-F-155 | 50 | 3 | 12.4 | 5.5 | 0.4 |
| Ti-Beta-F-133 | 50 | 3 | 15.9 | 7.4 | 0.5 |
| Ti-Beta-OH | 50 | 3 | 7.2 | 4.3 | 0.6 |
| Zr-Beta-F | 100 | 3 | 20.5 | 5.3 | 0.3 |
| Hf-Beta-F | 50 | 3 | 23.2 | 3.3 | 0.1 |

[a] Catalyst loading per volume of 5 wt% glucose reactant solution (mg catalyst (mL solution)$^{-1}$).
[b] Reported selectivities reflect the ratio of sorbose to fructose present in solution after reaction.
[c] Not detectable (<0.3% conversion).

FIG. 6

Table 3. Reaction conditions, conversions, and selectivities at 373 K for Ti-containing zeolite and zeotype materials which reflect solution compositions studied during $^{13}$C NMR experiments.

| Sample | Catalyst/Solution Ratio[a] | Reaction Time (h) | $X_{fructose}$ | $X_{sorbose}$ | Selectivity[b] |
|---|---|---|---|---|---|
| Ti-MCM-41 | 100 | 6 | n.d.[c] | n.d.[c] | |
| Ti-CON | 50 | 1 | 1.6 | 3.4 | 2.1 |
| Ti-MFI | 100 | 6 | 0.0 | 2.1 | >10 |
| Ti-MFI-NS | 100 | 6 | 2.6 | 6.0 | 2.3 |
| Ti-CHA | 100 | 6 | n.d.[c] | n.d.[c] | |

[a] Catalyst loading per volume of 5 wt% glucose reactant solution (mg catalyst (mL solution)$^{-1}$).
[b] Reported selectivities reflect the ratio of sorbose to fructose present in solution after reaction.
[c] Not detectable (<0.3% conversion).

FIG. 7

Table 4 Fructose and sorbose reaction rates (per Ti) and selectivities at 373 K for Ti-containing zeotype materials.

| Sample | Catalyst/Solution Ratio[a] | Fructose formation rate[b] | Sorbose formation rate[b] | Initial Selectivity[c] |
|---|---|---|---|---|
| Ti-MCM-41 | 100 | n.d.[d] | n.d.[d] | |
| Ti-Beta | 100 | $1.03 \times 10^{-3}$ | $0.40 \times 10^{-3}$ | 0.4 |
| Ti-CON | 50 | $1.69 \times 10^{-4}$ | $3.65 \times 10^{-4}$ | 2.2 |
| Ti-MFI | 100 | n.d.[d] | $5.33 \times 10^{-5}$ | >10 |
| Ti-MFI-NS | 100 | $2.16 \times 10^{-5}$ | $7.27 \times 10^{-5}$ | 3.4 |
| Ti-CHA | 100 | n.d.[d] | n.d.[d] | |

[a] Catalyst loading per volume of 5 wt% glucose reactant solution (mg catalyst (mL solution)$^{-1}$).
[b] Units are [mol product (mol Ti)$^{-1}$ s$^{-1}$].
[c] Selectivities calculated as the ratio of initial sorbose formation rate to initial fructose formation rate.
[d] Not detectable (<0.3% conversion).

FIG. 8

PROCESSES FOR PREPARING SORBOSE FROM GLUCOSE

CROSS-REFERENCE TO RELATED APPLICATIONS

This application claims the benefit of U.S. Provisional Application No. 62/803,719 filed Feb. 11, 2019, the contents of which are incorporated herein by reference.

BACKGROUND OF THE INVENTION

The present invention generally relates to glucose isomerization. The invention particularly relates to direct isomerization of glucose to sorbose.

Biomass and sugar upgrading involves a series of reaction pathways to form a wide variety of chemical monomers, fuels, and pharmaceuticals and high-value health supplements from renewable feedstocks. Vitamin C is one such health supplement with approximately 105 tons produced each year from ascorbic acid. Current vitamin C synthesis pathways follow the Reichstein process composed of the reduction of glucose to sorbitol via hydrogenation over nickel-based catalysts and the selective oxidation of sorbitol to sorbose over metalloenzyme catalysts. Sorbose can then be selectively oxidized over platinum catalysts to form ascorbic acid, a direct precursor to vitamin C.

Lewis acidic zeolites of predominantly siliceous materials and isomorphously substituted framework tetravalent metal ($M^{4+}$) heteroatoms (M-Beta) are a promising class of catalytic materials for biomass upgrading reactions from renewable reactant sources. These materials can confine isolated Lewis acidic active sites within microporous reaction environments which prevent intraporous diffusion of larger reactant molecules (reactant shape selectivity) and can selectively generate desired products by sterically hindering reaction pathways using the siloxane domains of channels (product shape selectivity). For example, U.S. Pat. No. 9,255,120 to Davis et al. discloses processes for the direct isomerization of glucose to sorbose mediated by Lewis acidic and/or $Zr^{4+}$ centers incorporated into the framework of silica zeolite beta (Ti-Beta or Zr-Beta). In Davis et al, Beta-type zeolites (with Ti/Zr/Hf) were shown to selectively form sorbose over fructose/mannose by a ratio of less than 2 (see Table 1 of Davis et al.). The contents of Davis et al. in their entirety are incorporated herein by reference. Other glucose-sorbose isomerization reaction pathways are generally unknown without the significant formation of undesirable side products.

There remains a desire for processes capable of converting glucose to sorbose with an increased sorbose selectivity, for example, relative to processes that use catalysts such as Ti-Beta zeolites.

BRIEF DESCRIPTION OF THE INVENTION

The present invention provides processes suitable for converting glucose to sorbose with tailored selectivity.

According to one aspect of the invention, a process for preparing sorbose from glucose includes contacting glucose with a silica-containing structure that includes a zeolite having a topology of a 10-membered ring or smaller and Lewis acidic $M^{4+}$ framework centers, wherein M is Ti, Sn, Zr, or Hf. Contacting the glucose is conducted under reaction conditions sufficient to isomerize the glucose to sorbose.

Other aspects of the invention include the process described above, wherein the structure comprises Ti-CON (Ti-SSZ-33), Ti-MFI (TS-1), or nanosheet Ti-MFI (Ti-MFI-NS).

Technical effects of the process described above preferably include the ability to convert glucose to sorbose with an increased sorbose selectivity relative to previously disclosed catalysts such as Ti-Beta zeolites. The process develops and utilizes new zeolite framework types (containing active metal sites such as Ti, Zr, Hf) that dramatically increase the selectivity to sorbose over other sugar isomer products, for example, in comparison to the selectively reported in U.S. Pat. No. 9,255,120 to Davis et al. The new zeolite frameworks (specifically with 10-MR as the largest ring size) are capable of increasing the selectivity to sorbose to greater than 10, wherein essentially no fructose/mannose is formed. The zeolite framework pore structure is identified and utilized as a means to maximize the selectivity to sorbose over other competing isomer products.

Other aspects and advantages of this invention will be appreciated from the following detailed description.

BRIEF DESCRIPTION OF THE DRAWINGS

FIG. 1 includes $^{13}C$ NMR spectra of product solutions collected after reaction on Ti-Beta-F-155, Zr-Beta, and Hf-Beta zeolites. Spectra collected on glucose, sorbose, and fructose standards are given for comparison. Peaks centered at 61.6 and 70.2 ppm reflect sorbose presence and peaks centered at 67.3 and 97.6 ppm reflect fructose in solution. Spectra of product solutions after reaction on all Ti-Beta zeolites are similar.

FIG. 4 includes $^{13}C$ NMR spectra of product solutions collected after reaction on Ti-CON, Ti-MFI, and Ti-MFI-NS zeolites. Spectra collected on glucose, sorbose, and fructose standards are given for comparison. Peaks centered at 61.6 and 70.2 ppm reflect sorbose presence and peaks centered at 67.3 and 97.6 ppm reflect fructose in solution. Spectra of product solutions after reaction on all Ti-Beta zeolites were similar.

FIG. 5 (Table 1) includes site and structural characterization data for Lewis acidic zeolite and zeotype samples from investigations leading to the present invention.

FIG. 6 (Table 2) includes reaction conditions, conversions, and selectivities at 373K for M-Beta zeolites from investigations leading to the present invention which reflect solution compositions studied during $^{13}C$ NMR experiments.

FIG. 7 (Table 3) includes reaction conditions, conversions, and selectivities at 373K for Ti-containing zeolite and zeotype materials from investigations leading to the present invention which reflect solution compositions studied during $^{13}C$ NMR experiments.

FIG. 8 (Table 4) contains values of initial product formation rates and initial selectivity to sorbose.

DETAILED DESCRIPTION OF THE INVENTION

Figure 1:
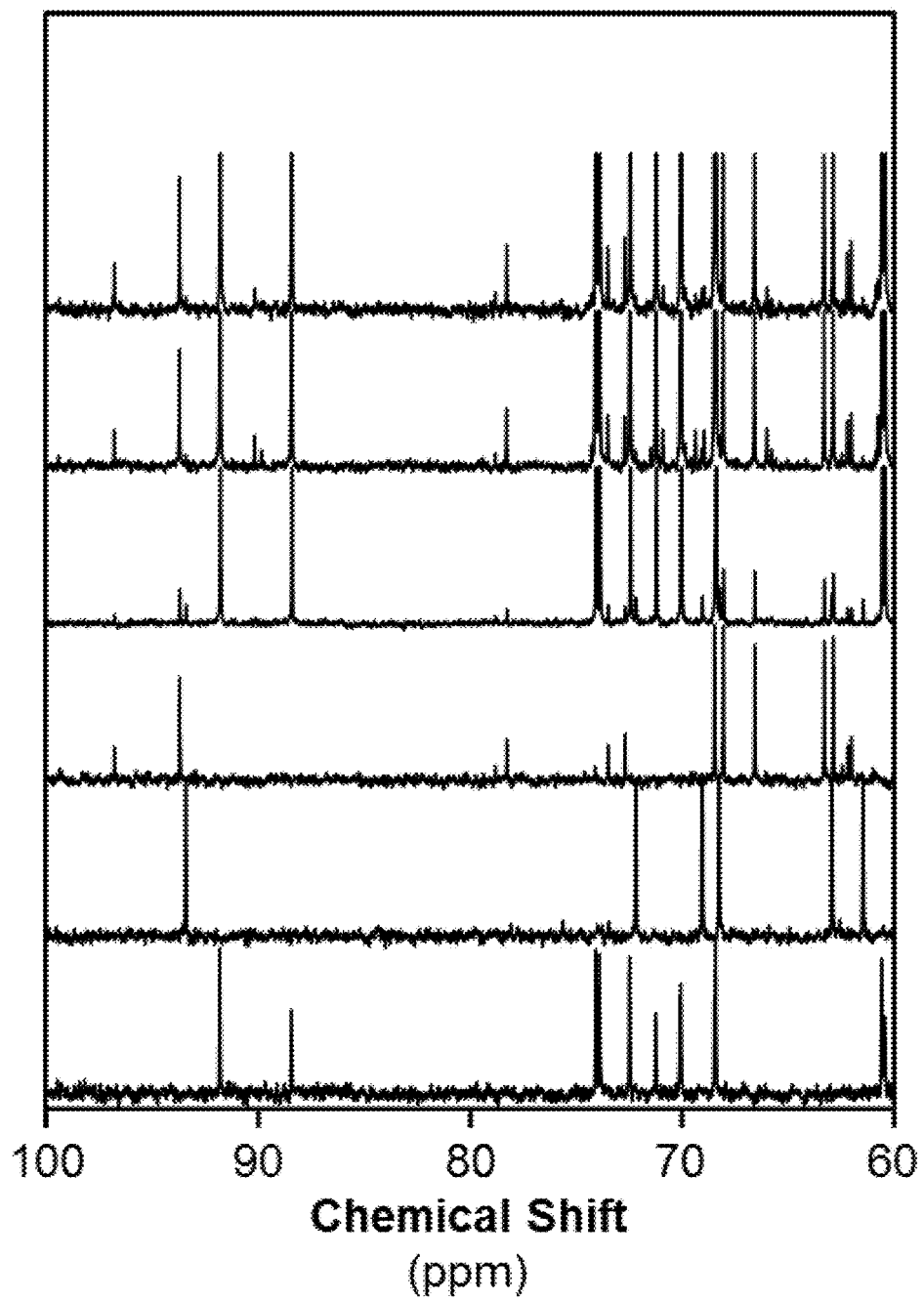

Disclosed herein are processes for the catalytic conversion of glucose to sorbose that include direct isomerization of glucose to sorbose which is mediated by Lewis acidic $M^{4+}$ ($Ti^{4+}$, $Sn^{4+}$, $Zr^{4+}$, $Hf^{4+}$) centers incorporated into the framework of silica zeolite. In certain embodiments, the processes use silica-containing structures having Lewis acid centers tailored for increased sorbose selectivity relative to previously disclosed catalysts such as Ti-Beta zeolites.

Nonlimiting embodiments include processes for preparing sorbose from glucose that involve contacting glucose with a silica-containing structure comprising a zeolite having a topology of a 10-membered ring or smaller and Lewis acidic $Ti^{4+}$ framework centers. Glucose contact was conducted under reaction conditions sufficient to isomerize the glucose to sorbose. In certain embodiments, the sorbose was L-(−)sorbose and the glucose was D-(+)-glucose. Exemplary but nonlimiting structures include zeolites comprising Ti-CON (Ti-SSZ-33), Ti-MFI (TS-1), and nanosheet Ti-MFI (Ti-MFI-NS). These Lewis acidic Ti-zeolites have smaller micropore sizes than Ti-Beta and, as indicated by the investigations discussed below, were observed to result in enhancements in selectivities toward sorbose of more than 10 to 30 times that of competing isomer products such as fructose. Other Lewis acidic T-zeolites that may be suitable include Ti-MWW (10-MR) and Ti-MOR (12-MR).

Nonlimiting embodiments of the invention will now be described in reference to experimental investigations leading up to the invention. These investigations explored catalytic requirements of Lewis acidic active sites and confining environments for selective glucose-sorbose isomerization. Specifically, sorbose formation rates on Beta zeolites with varied Lewis acid site identity ($M^{4+}$=Ti, Sn, Zr, Hf) were compared to suggest the electronic and site configuration requirements that stabilize intermediates and transition states that are kinetically-relevant for sorbose formation. Additionally, Lewis acidic zeolites and zeotypes were synthesized with varied topology ranging between 6- and 14-membered ring (14-MR) channels, synthetic and treatment history, and hydrophobicity prior to aqueous-phase kinetic studies (1 wt %, 373K) to quantify sorbose formation rates and initial sorbose-fructose selectivities.

Catalyst Sample Synthesis:

As understood by those of ordinary skill in the art, M-Beta zeolites (sometimes referred to herein as "catalysts"), including Ti—, Zr—, and Hf-Beta zeolites discussed below, are Framework Type *BEA zeolites, can be synthesized using OH⁻ ions and F⁻ ions (which exhibit hydrophilic and hydrophobic properties, respectively) as counter anions of the structure directing agent, and have ring sizes (#T-atoms) of 12, 6, 5, or 4.

M-Beta zeolite catalysts containing tetravalent metal ($M^{4+}$) heteroatoms (M-Beta) were made via both hydrothermal and grafting synthesis procedures. Hydrothermal Ti-Beta zeolites with fluoride mineralizing agents (Ti-Beta-F) were synthesized using gel molar ratios of 1 TEOS/X TEOTi/0.55 TEAOH/7.5 $H_2O$/0.55 HF where X=0.008-0.013. 21.77 g of tetraethylammonium hydroxide (TEAOH, 35%, Sigma Aldrich) was diluted in 12.72 g deionized water in a perfluoroalkoxy alkane (PFA) jar that was covered and stirred at ambient temperature for 15 minutes. 20.00 g of tetraethylorthosilicate (TEOS, 98%, Sigma Aldrich) was then added and stirred for 45 minutes prior to the addition of about 0.2 g of tetraethyl orthotitanate (TEOTi, 99.99%, Alfa Aesar). The jar was then sealed to stir for 12 h. The resulting solution was then exposed to air to evaporate ethanol and excess water to achieve the desired molar ratios. 2.16 g of hydrofluoric acid (HF, 48%, Alfa Aesar) was added to the resulting gel prior to the addition of 0.28 g of Si-Beta seeds. The resulting gel was then loaded into a 45 mL Teflon liner inside of a stainless steel autoclave (Parr Instruments) and placed into a forced convection oven (Yamato DKN-402C) at 413K for 21 days while rotating (60 rpm). Recovered solids were then removed from the oven and liner and washed with about 150 cm³ of deionized water per gram of recovered solid. The recovered solids were isolated by centrifugation and dried for 16 h at 373K in air. Organic occluded within the solids were removed through 10 h of high temperature oxidative treatment in flowing dry air (1.67 cm3 s⁻¹ $g_{cat}^{-1}$, 99.999% UHP, Indiana Oxygen) at 823K (0.0167 K s⁻¹). The synthesis of Beta zeolites with hafnium or zirconium Lewis acid sites using fluoride mineralizing agents (Hf-Beta-F and Zr-Beta-F, respectively) was achieved by replacing the TEOTi reagent in the above synthesis with hafnium tetrachloride ($HfCl_4$, 99.99%, Sigma Aldrich) dissolved in ethanol or zirconium oxychloride octahydrate ($ZrOCl_2$, 98%, Sigma Aldrich) at equivalent molar ratios.

Beta-OH materials were also synthesized without the use of fluoride mineralizing agents as precursor materials for metal heteroatom grafting procedures. Al-Beta zeolites were synthesized using gel molar ratios of 1 $SiO_2$/0.0167 AlPO/ 0.028 NaOH/0.36 TEAOH/13.24 $H_2O$. 22.69 g of TEAOH was diluted in 35.74 g of deionized water and stirred for 15 minutes. Next, 30 g of Ludox HS-30 colloidal silica (30%, Sigma Aldrich) was added and the solution was homogenized for 45 minutes. Separately, 0.171 g of NaOH (98%, Avantor) was dissolved in deionized water prior to the addition of 1.04 g of aluminum isopropoxide (AlPO, 98%, Aldrich). The resulting solution was then added dropwise to the silica-containing solution and sealed for overnight homogenization. Excess water was evaporated off to achieve the target molar ratios prior to loading the gel into 45 mL Teflon liners and heating for 6 days at 413K in a stainless steel autoclave. The solids were then recovered, washed, dried, and oxidatively treated as per the M-Beta zeolites above. Framework aluminum atoms were then removed by heating 0.5 g of Al-Beta to 353K in 12.5 cm³ of concentrated nitric acid (69%, Avantor). Dealuminated solids were thoroughly washed in water (about 200 cm³ (g zeolite)⁻¹), isolated via centrifugation, and dried overnight at 373K. Residual aluminum presence was undetectable (Si/Al>1500).

MFI zeolite catalysts (MFI framework type zeolites having ring sizes (#T-atoms) of 10, 6, 5, or 4) containing Group 4 heteroatoms were made via hydrothermal synthesis procedures. Ti-MFI (TS-1) was synthesized using gel molar ratios of 1 $SiO_2$/0.076 TEOTi/1 $NH_4F$/0.25 TPABr/31.56 $H_2O$. Ammonium fluoride (NH4F, 98%, Sigma Aldrich) and tetrapropylammonium bromide (TPABr, 98%, Sigma Aldrich) were diluted in 31.46 g of deionized water and stirred for 15 minutes in a covered PFA jar. 3 g of fumed silica (Cab-o-sil $SiO_2$, 99.9%, Cabot) was then added to the synthesis gel and stirred for 45 minutes prior to the addition of 0.076 g of TEOTi. The resulting gel was covered and stirred overnight before evaporating evolved ethanol and excess water to achieve the desired molar ratios. The resulting gel was loaded into a 45 mL Teflon liner in a stainless steel autoclave and heated to 413K for 14 days while rotating at 60 rpm. Recovered solids were then removed from the oven, washed, isolated by centrifugation, and dried for 16 h at 373 K in air. Organic occluded within the solids were removed through 10 h of high temperature oxidative treatment in flowing dry air at 823 K (0.0167 K s⁻¹).

Nanosheet Ti-MFI (Ti-MFI-NS) zeolite catalysts were prepared as single-unit-cell thick titanium-containing zeolites synthesized through the use of a [$C_{18}H_{37}$—

N+(CH$_3$)$_2$—C$_6$H$_{12}$—N+(CH$_3$)$_2$—C$_6$H$_{13}$]OH$_2$ surfactant, denoted C$_{18-6-6}$OH$_2$. The final gel molar ratios were 1 SiO$_2$/0.07 C$_{18-6-6}$OH$_2$/0.01 TBOT/60 H$_2$O. 25.19 g of 0.13 M aqueous C$_{18-6-6}$OH$_2$ solution was diluted in 30.16 g of deionized H$_2$O in a covered PFA jar and stirred for 10 minutes prior to the addition of 10 g of TEOS followed by 30 minutes of stirring. 0.16 g of tetrabutyl orthotitanate (TBOT, >99.99%, Alfa Aesar) was then added to the synthesis gel prior to capping the jar and stirring overnight. The resulting gel was exposed to air to allow for excess water and evolved ethanol and butanol evaporation to achieve target molar ratios. The gel was loaded into a 45 mL Teflon liner and stainless steel autoclave prior to heating to 413K for 10 days while rotating at 60 rpm. Recovered solids were washed with deionized water, isolated by centrifugation, and dried for 16 h at 373 K in air. Organic occluded within the solids were removed through 10 h of high temperature oxidative treatment in flowing dry air at 823 K (0.0167 K s$^{-1}$).

Ti-CON zeolite catalysts (CON framework type zeolites having ring sizes (#T-atoms) of 12, 10, 6, 5, or 4) were prepared via post-synthetic grafting procedures of titanium precursors into deboronated CON. B-CON was synthesized using 1,4-bis(1-cyclohexyl-1,4-pyrrolidin-1-yl)butane (BCPB) as the structure directing agent and a final gel molar ratio of 1 SiO$_2$/2 NaOH/0.1 BCPB/0.0055 Na$_2$B$_4$O$_7$/45.6 H$_2$O. 3.62 g of aqueous BCPB (9.9%) was diluted in 7.39 g of deionized water and 0.72 g of 1 M NaOH (99.99%, Avantor) in a PFA liner and stirred for 5 minutes. 0.036 g of sodium tetraborate decahydrate (Na$_2$B$_4$O$_7$, 99.99%, Sigma Aldrich) was then added and stirred for 5 minutes prior to the addition of 0.54 g of fumed silica (Cab-o-sil SiO$_2$, 99.9%, Cabot). The resulting gel was stirred in a covered PFA jar for 1 h before loading into a 23 mL Teflon liner and encased in a stainless steel autoclave. The synthesis gel was heated to 433K for 7 days rotating at 60 rpm. Recovered solids were washed in water and acetone, isolated by centrifugation, dried overnight at 373 K, and treated at 823 K in oxygen for 10 h. B-CON zeolites were treated at 353K in 25 cm$^3$ of concentrated nitric acid per gram of zeolite for 16 h to remove boron heteroatoms from the framework. Deboronated solids were washed with copious amounts of water (about 200 cm$^3$ (g zeolite)$^{-1}$), isolated via centrifugation, and dried overnight at 373K.

Dealuminated Beta (de-Al-Beta) and deboronated CON (de-B-CON) were then subjected to post-synthetic grafting procedures to incorporate titanium heteroatoms into the framework. Typically, about 0.5 g of zeolite were loaded into a three-neck, 0.5 L round-bottom flask with a septum stopper on one opening. The flask was attached to a Schlenk line and De-B-CON precursors were dried overnight (423K) under vacuum (about 0.005 kPa). In a separate flask, dichloromethane was dried over molecular sieves (Type 3A, Grade 562, 4-8 mesh, W.R. Grace) in an inert atmosphere (Ar, Indiana Oxygen, 99.999%) for 72 h. about 0.5 cm$^3$ of 1 M titanium tetrachloride in dichloromethane (TiCl$_4$, 99.99%, Sigma Aldrich) was transferred to a pear-shaped flask and dried dichloromethane dichloromethane were transferred to the round-bottom flask via moisture-free cannula transfer. The resulting solution was heated to 383K for 7 h under reflux conditions in an argon atmosphere. The resulting solids were then recovered via centrifugation, washed with about 120 cm$^3$ of methanol (99.99%, Sigma Aldrich) per gram of zeolite, and dried overnight at 373K. Solids were treated in flowing air (1.67 cm3 s$^{-1}$ g$_{cat}^{-1}$, 99.999% UHP, Indiana Oxygen) to 473K (0.05 K s$^{-1}$) for 6 h and then heated further to 823K (0.05 K s$^{-1}$) for an additional 6 h.

Ti-CHA was synthesized hydrothermally as follows. 40 g of ethanol (200 proof, Koptec) and 25 g of TEOS were added to a PFA jar and stirred for 300 s at ambient conditions. Next, a solution containing 0.601 g of TEOTi dissolved in 10 g of ethanol was added dropwise to the solution containing ethanol and TEOS and stirred for 300 s at ambient conditions. Afterward, 0.577 g of hydrogen peroxide (H$_2$O$_2$, 30 wt %, Alfa Aesar) were added and stirred for 900 s. Next, 42.329 g of an aqueous N,N,N-trimethyl-1-adamantylammonium hydroxide solution (TMAdaOH, 25 wt %, Sachem) were added dropwise, where the solution gelatinized after the addition of 15 to 20 g of TMAdaOH and required the addition of 49.920 g of deionized water and manual stirring with a Teflon spatula until the solution was uniform. The rest of the TMAdaOH was added immediately after and the solution was covered and stirred for 24 h at ambient conditions. Ethanol and excess water were evaporated from the obtained solution to reach the desired H$_2$O/SiO$_2$ molar ratio of 3. The resulting powder was rehydrated with 80 g of water, stirred for 24 h, and dehydrated again to obtain the desired H$_2$O/SiO$_2$ molar ratio of 3. Finally, 2.69 g of HF were added dropwise to the synthesis powder and stirred manually for 300 s. Residual HF was allowed to evaporate for 900 s. The final molar ratio of the gel solution was 1 SiO$_2$/0.014 TiO$_2$/0.43 TMAdaOH/0.38 HF/3 H$_2$O. The gel was loaded into a 45 mL Teflon liner and stainless steel autoclave prior to heating to 423 K for 2 days while rotating at 40 rpm. Recovered solids were washed thoroughly with water and acetone, isolated by centrifugation, and dried for 16 h at 373 K in air. Organic occluded within the solids were removed through 10 h of high temperature oxidative treatment in flowing dry air at 823 K (0.0167 K s$^{-1}$).

Characterization of Catalytic Materials:

Bulk crystal topologies of synthesized materials were determined from powder X-ray diffraction (XRD) patterns collected on a Rigaku SmartLab X-ray diffractometer using a Cu Kα source (1.76 kW) measured from 4-40° (2θ, 0.00417° s$^{-1}$). Micropore volumes were calculated from N$_2$ adsorption isotherms (77K) collected on a Micromeritics ASAP 2020 Surface Area and Porosity Analyzer via linear extrapolation from the beginning of the mesopore filling regime (about 0.05-0.30 P/P$_0$). All micropore volumes align with known micropore volumes of each desired zeolite topology.

Bulk titanium concentrations were determined via atomic absorption spectroscopy (AAS, PerkinElmer AAnalyst 300 Atomic Absorption Spectrometer). about 0.2 g of solid were dissolved in about 2 g of hydrofluoric acid (48 wt %), left overnight, then diluted with about 50 g of deionized water. Absorbances were measured in a reducing acetylene and nitrous oxide flame at 399.9 nm and compared to calibration curves from titanium solutions of known composition.

Nitrogen (N$_2$, 77K) and argon (Ar, 87K) adsorption isotherms were collected using a Micromeritics ASAP2020 Surface Area and Porosity Analyzer on about 0.03 g of sample pelleted and sieved to maintain uniform particle diameters between 180 and 250 µm. Samples were degassed prior to analysis by heating to 393K (0.0167 K s$^{-1}$) under vacuum (<0.005 Torr) for 2 h then heating to 623K (0.0167 K s$^{-1}$) under vacuum for 8 h. Micropore volumes were calculated from the semi-log derivative analysis of N$_2$ (or Ar) adsorption isotherms (δ(V$_{ads}$/g)/δ(log(P/P$_0$)) vs. log ($_{P/P0}$)).

Glucose Isomerization Kinetic Investigations:

Kinetic measurements were carried out in 10 mL thick-walled batch reactors (VWR) with 0.01-0.1 g of sample and 5 wt % aqueous-phase D-glucose (Sigma-Aldrich, >99.5%) solutions. Distilled water (18.2 MΩ) was pH-controlled (pH 3) with hydrochloric acid (HCl, Macron, 37 wt %) and mixed with D-glucose to the desired weight percent. Solutions were filtered through 0.2 μm PTFE filters (VWR) and loaded into 2 mL glass vials capped with a PTFE/silicone septum (Waters) until full. Batch reactors were loaded with a stir bar and about 0.01-0.1 g of catalyst and sealed with a crimp top (PTFE/silicone septum, Agilent). Reactant solution vials and reactors were separately heated (353-393K) for 600 s atop a digital stirred hotplate (IKA RCT basic) prior to injecting about 1 cm$^3$ of preheated reactant solution into the capped reactors. Reactors were maintained at temperature (353-393K, autogenous pressure, 750 rpm) for various time intervals (1800-21600 s) prior to quenching in an ice bath to stop the reaction.

Product solutions were filtered (0.2 μm PTFE filters), diluted to 1 wt % with deionized water, and mixed with an internal quantification standard of a 1 wt % aqueous D-mannitol (Sigma Aldrich, 98 wt %) solution. Product separation and quantification were performed using a high performance liquid chromatograph (Agilent 1260) equipped with a Hi-Plex Ca column (7.7×300 mm, 8 μm particle size, 0.01 cm$^3$ s$^{-1}$ aqueous mobile phase, 353K) and inline evaporative light scattering detector (Agilent 1290). Quantification was performed using separate calibration curves for individual sugar species. All reported rates and selectivities correspond to conversions of less than 5% and match initial rate measurements from transient kinetic measurements.

Isotopic labeling studies to identify isomerization products were performed by reacting 1 cm$^3$ of a 5 wt % aqueous D-glucose-D2 (Cambridge Isotope Laboratories, 98% 2-D) solution and 0.01-0.04 g of catalytic solids (373K, 1800-21600 s) prior to quenching, filtering product solutions, and separating as described above. Product solutions were prepared by freezing in liquid N$_2$ (77K) and removing water via freeze-drying on a Labconco FreeZone lyophilizer (<0.01 Torr, 36 h). Dried sugars were then dissolved in 0.06 cm$^3$ of D$_2$O (Cambridge Isotope Laboratories, 99.9%) and loaded into NMR tubes (Wilmad LabGlass, 5 mm thin wall, 7 in., 500 MHz) for NMR analysis. $^{13}$C NMR spectra were collected at ambient temperature on a Bruker ARX500 spectrometer equipped with a 5 mm QNP probe by averaging 256-1500 scans acquired at about 0.3 scans per second.

Sorbose Formation on Beta Zeolites of Varied Lewis Acidic Heteroatom Identity:

M$^{4+}$-containing Beta zeolites (M$^{4+}$=Ti, Zr, Hf) were synthesized via hydrothermal syntheses or post-synthetic grafting techniques to remove aluminum heteroatoms from framework positions and subsequently graft framework silanol nests with M$^{4+}$ heteroatoms with relevant structural data summarized in Table 1 (FIG. 5). Samples identified in Table 1 and discussed below are denoted as Ti-IZA-X, where IZA stands for the IZA code of each zeolite topology and X represents the Si/Ti molar ratio. Powder X-ray diffraction patterns and micropore volume measurements derived from N$_2$ adsorption isotherms (77K) were consistent with the Beta topology. Micropore volumes and measured Si/M ratios are also reported in Table 1.

Figure 2:
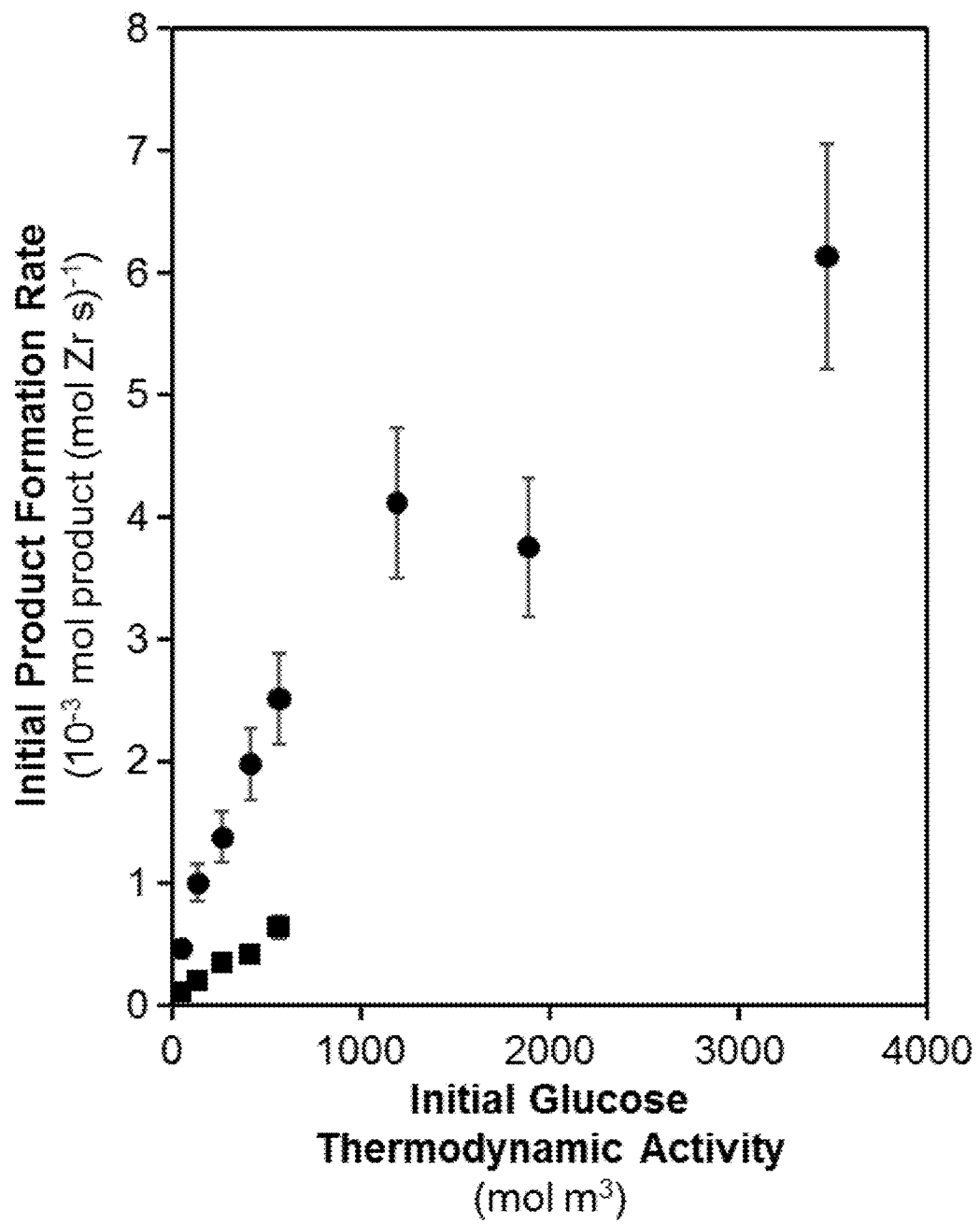
FIG. 2 includes a plot of initial glucose-fructose (circles) and glucose-sorbose (squares) isomerization rates on Zr-Beta-150 (373K, per mol Zr) as a function of initial glucose concentration.

Aqueous-phase glucose isomerization measurements on Ti-Beta-F, Ti-Beta-OH, Zr-Beta-F, and Hf-Beta-F zeolites indicated the formation of both fructose and sorbose isomers. FIG. 1 shows $^{13}$C NMR spectra of product solutions collected after reaction on each M-Beta-F zeolite. $^{13}$C NMR spectra were compared against known standards for glucose, fructose, and sorbose. Peaks centered at 61.6 and 70.2 ppm reflect sorbose, and peaks centered at 67.3 and 97.6 ppm reflect fructose. Both sorbose and fructose were observed in each spectrum, yet with differing intensities reflecting the different sorbose-fructose selectivities given in Table 2 (FIG. 6). Kinetic measurements of initial glucose-sorbose isomerization rates on Zr-Beta and Hf-Beta zeolites require higher glucose conversions due to low sorbose-fructose selectivities and were collected at non-differential glucose conversions; however, transient batch reactor studies on sorbose and fructose formation rates indicated that the two glucose isomers are parallel products and that sorbose is not a secondary product of fructose. Further, FIG. 2 shows initial glucose-fructose and glucose-sorbose formation rates on Zr-Beta-F as a function of initial glucose concentration. Fructose and sorbose formation rates showed a first-order dependence on glucose concentration and increase with one another, consistent with both glucose isomers formed as parallel products on Zr sites. This suggests that Lewis acidic Zr (and by extension Hf) sites behave similarly to Lewis acidic Ti sites for forming both fructose and sorbose as parallel reaction products.

Figure 3:
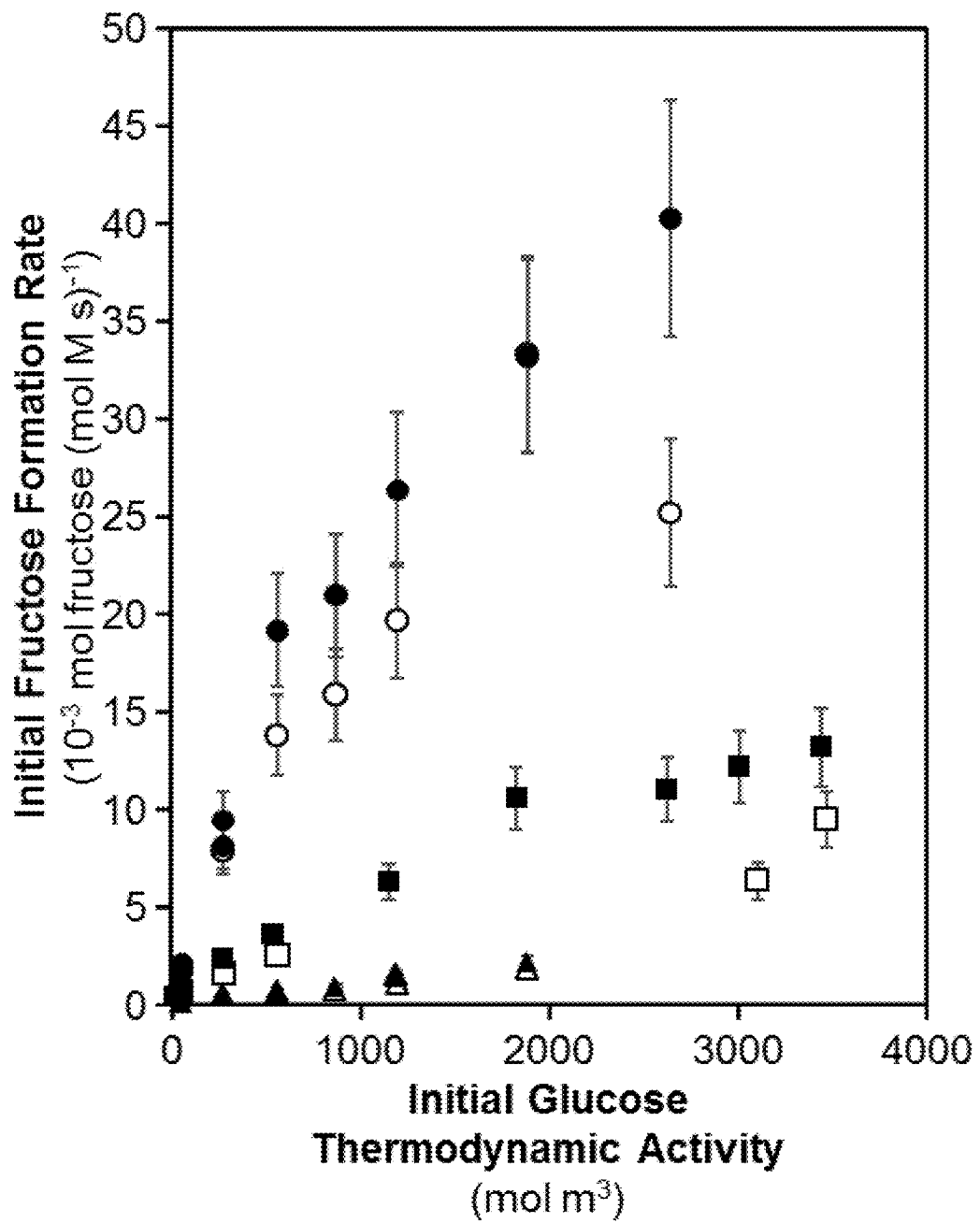
FIG. 3 includes a plot of initial glucose-fructose and glucose-sorbose isomerization rates on Zr-Beta-170 (open) and Hf-Beta (closed) per mol M at 353K (triangles), 373K (squares), and 393K (circles) as a function of initial glucose concentration.
Figure 4:
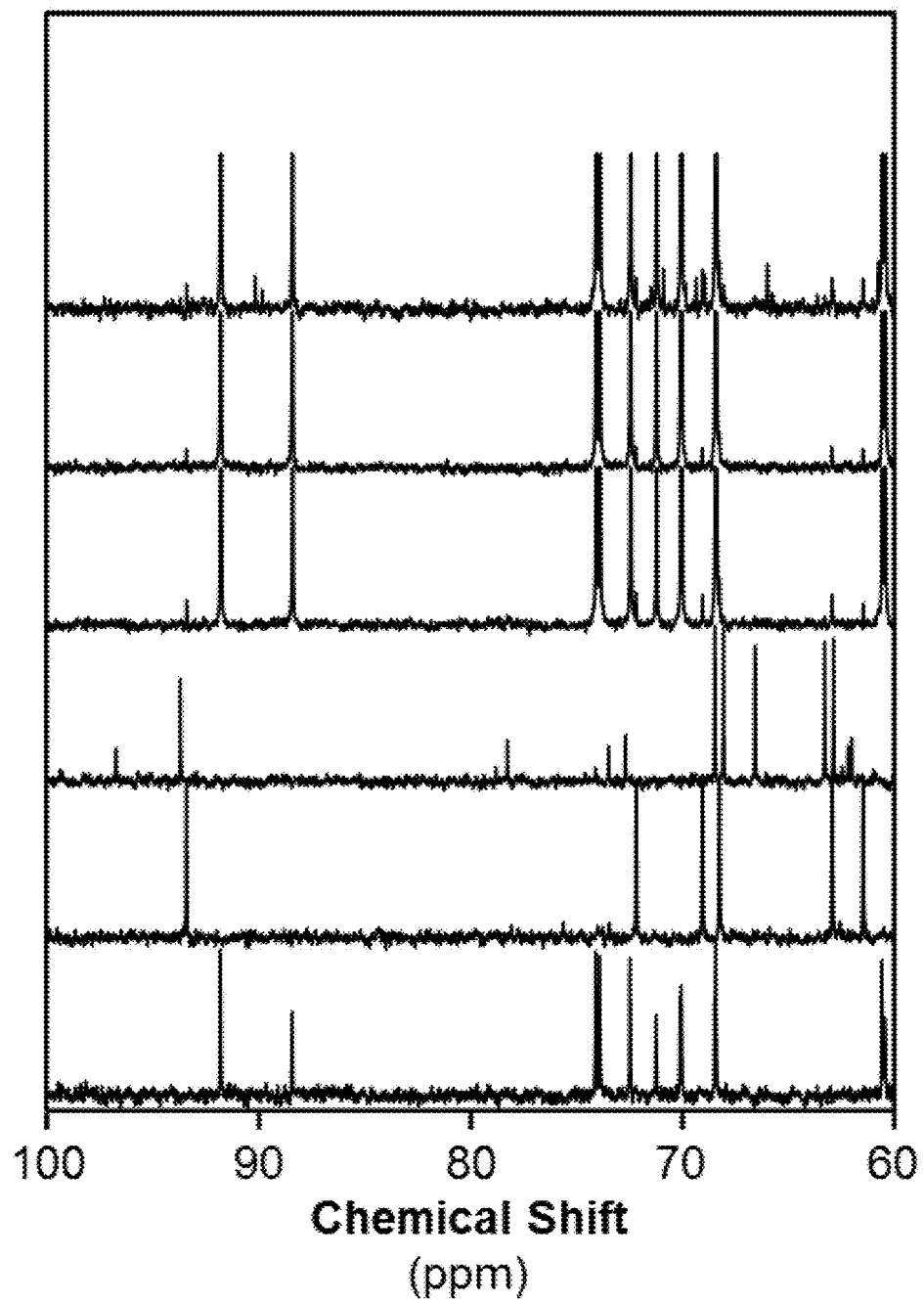

Aqueous-phase glucose-fructose (and glucose-sorbose on Ti-Beta) isomerization rates were first-order in glucose concentration at dilute glucose concentrations on Ti-Beta (1-20 wt %, 368-383K, per Lewis acidic Ti) and Sn-Beta (1-10 wt %, 373K, per open Sn) zeolites when Lewis acid sites were confined within either hydrophobic or hydrophilic confining environments. First-order rate constants on Ti-Beta and Sn-Beta zeolites reflect free energy differences between hydride shift transition states and two water molecules adsorbed onto each Lewis acid site. FIG. 3 shows initial aqueous-phase glucose-fructose and glucose-sorbose isomerization rates (353-393K, 1-50 wt %) on Zr-Beta and Hf-Beta zeolites as a function of glucose concentration. Initial isomerization rates were first-order in glucose concentration at dilute glucose concentrations on Zr-Beta and Hf-Beta materials, implying a similar kinetic regime to that observed on Sn-Beta and Ti-Beta materials which measures free energy differences between hydride shift transition states and two bound water intermediates.

Initial glucose-fructose and glucose-sorbose rates (353-393K) on Zr-Beta-F and Hf-Beta-F both shift from first-order to zero-order in glucose concentration at higher glucose concentrations. The presence of these two distinct kinetic regimes is similar to aqueous-phase glucose isomerization behavior on Ti-Beta zeolites, which undergoes a nearly isoenergetic transition in the identity of the most abundant reactive intermediate (MARI) from two-water-bound to glucose-bound intermediates. Both fructose and sorbose formation rates shift from first-order to zero-order at lower glucose concentrations on Zr-Beta-F and Hf-Beta-F, however, indicating lower water adsorption enthalpies on Lewis acidic Zr and Hf sites than on Ti sites.

Overall, sorbose formation was observed on other Lewis acid sites besides Ti, indicating that aqueous-phase glucose-sorbose isomerization does not specifically require a Lewis acidic Ti site. The higher sorbose-fructose selectivity observed on Ti-Beta zeolite catalysts and higher initial sorbose formation rates, however, suggested that titanosilicate materials are an ideal case study for investigating the catalytic consequences of zeolitic confining environments on sorbose formation.

Sorbose Formation on Ti-Containing Zeolites and Zeotypes of Varying Topology:

Sorbose formation has been previously observed in both methanol and water solvents on Ti-Beta zeolites, yet no sorbose formation was detectable on amorphous titanosilicate (TiO$_2$—SiO$_2$) materials that do not contain Lewis acidic active sites confined within microporous environments. At first glance, this may imply the requirement of a microporous confining environment to facilitate Lewis acid catalyzed glucose-sorbose isomerization. Ti-containing zeolites and zeotypes were synthesized with a wide range of confining environments and microporous ring sizes (6-14 MR) by altering the zeolite topology. XRD patterns of titanosilicate materials (Ti-MCM-41, Ti-CON, Ti-MFI, Ti-MFI-NS, and Ti-CHA) match previously reported patterns for each desired topology and micropore volumes derived from $N_2$ adsorption isotherms (77K, Ar adsorption isotherm at 87K used for Ti-CHA) on all samples further indicated the presence of the intended topologies. These chosen topologies range from 6-MR voids (Ti-CHA) through mesoporous voids (Ti-MCM-41), but focused predominantly on titanosilicate materials with 10-MR and 12-MR channels.

Initial glucose-fructose and glucose-sorbose isomerization rates (373K, 5 wt %) were measured on each titanosilicate material as shown in Table 3 (FIG. 7). Samples were organized from largest to smallest micropore diameter for ease of comparison. Isomerization rates were negligible on mesoporous Ti-MCM-41, which contains mesopores (>1.5 nm) of substantially larger diameter than Ti-Beta. This kinetic behavior is similar to that of amorphous $TiO_2$—$SiO_2$, as the mesoporous confining environments were too large to stabilize bound glucose intermediates through van der Waals interactions, as otherwise observed on Ti-Beta.

Ti-CON has a three-dimensional pore system of 10-MR (0.55 nm diam.) and 12-MR (0.7 nm diam.) and shows higher sorbose-fructose selectivity (about 4×, Table 3) towards sorbose than Ti-Beta zeolites (about 0.5) that contains only 12-MR voids. Both sorbose and fructose were formed on the same Lewis acid sites on both materials, suggesting that either local differences in the confining 12-MR structure Ti-CON and Ti-Beta, or contributions from the 10-MR voids, were responsible for the increased sorbose selectivity on Ti-CON. Ti-MFI has 10-MR straight and sinusoidal channels, and their larger intersections, and also selectively forms sorbose. While the initial rates were extremely low on Ti-MFI, the selectivity to sorbose was substantially higher (>10) than on Ti-Beta (about 0.5). Higher sorbose selectivities (about 4×) were also observed on nanosheet Ti-MFI (Ti-MFI-NS) materials compared to Ti-Beta materials, but detectable fructose formation was observed concomitantly. Fructose formation on single unit cell thick Ti-MFI-NS cannot be formed within microporous voids, or in bulk solution, as this would have also been observed after reaction with Ti-MFI. Therefore, fructose formation on Ti-MFI-NS was catalyzed by Ti sites in mesoporous reaction environments, which were detected by the hysteresis behavior of the Ti-MFI-NS $N_2$, adsorption isotherm. This was corroborated by higher sorbose selectivity on Ti-CON, which has both 12-MR channels that facilitate both fructose and sorbose formation (as in the case of Ti-Beta) and 10-MR channels that selectively form sorbose (as in the case of Ti-MFI). Higher sorbose formation rates relative to fructose may therefore be expected assuming a random distribution of framework Ti sites in both 10-MR and 12-MR channels, yielding higher sorbose selectivities overall. This suggests that Lewis acid sites that were confined within microporous environments that approach the size of glucose (about 0.86 nm for ring-closed glucose) can more selectively stabilize 1,5-hydride shift transition states that form sorbose, while sites confined within larger micropores can stabilize hydride shift transition states that form both fructose and sorbose. Confining environments that were too large, however, such as the mesoporous voids of Ti-MCM-41 do not catalyze glucose isomerization at detectable rates, and those that were too small, as in the case of Ti-CHA materials (6 MR, 0.38 nm), prevent glucose adsorption within microporous voids and also do not catalyze glucose isomerization.

In the above described investigations, the active site and confining environment requirements for the selective aqueous-phase glucose-sorbose isomerization were investigated using a wide variety of Lewis acidic zeolite and zeotype materials. M-Beta zeolites (M=Ti, Zr, and Hf) were observed to catalyze fructose and sorbose formation (373K, 1-20 wt %), yet Zr and Hf resulted in lower sorbose-fructose selectivities by about 6 and 12 times, respectively, compared to Ti. Microporous materials containing framework Ti sites confined within 10-MR channels selectively form fructose over sorbose, indicating that tighter confinement stabilizes 1,5-hydride shift transition states that lead to glucose-sorbose isomerization over 1,2-hydride shift transition states that lead to glucose-fructose isomerization. This coupling of active site and confining environment to selectively mediate one stereoselective reaction pathway over other possibilities is reminiscent of metalloenzymes that regulate reactivity by combining metallic active sites, and structures of confining environments, to carry out selective catalytic reactions.

The investigations reported above showed that reaction conditions sufficient to isomerize the glucose to sorbose included temperatures of 353 to 393K, autogenous pressures, stirring speeds of about 750 rpm, and durations of 1800-21600 s. However, broader ranges for the process parameters are foreseeable, as any that lead to sufficient conversion of glucose could be used as identified from the technical literature. For example, as reported in U.S. Pat. No. 9,255,120 to Davis et al., foreseeable reaction temperatures include about 333 to about 473K. Moreover, pressures other than autogeneous pressures could be used (because the reaction is entirely a liquid-phase reaction), essentially any stirring speed (including zero rpm) could be used that will ensure contact between the liquid reactants and the solid catalyst (Cordon, Dominant Role of Entropy in Stabilizing Sugar Isomerization Transition States within Hydrophobic Zeolite Pores, J. Am. Chem. Soc. 2018, 140, 14244-14266), and durations of 0 to about 86400s could be used (Cordon et al., Deactivation of Sn-beta Zeolites Caused by Structural Transformation of Hydrophobic to Hydrophilic Micropores During Aqueous-phase Glucose Isomerization, Catal. Sci. Technol., 2019, 9, 1654-1668).

While the invention has been described in terms of specific or particular embodiments and investigations, it should be apparent that alternatives could be adopted by one skilled in the art. For example, the processes may use Lewis acidic zeolite and zeotype materials other than those noted, may use more than one Lewis acidic zeolite or zeotype material, process parameters such as temperatures and durations could be modified, and other methods of synthesizing the Lewis acidic zeolite and zeotype materials could be used. Accordingly, it should be understood that the invention is not necessarily limited to any embodiment described herein. It should also be understood that the phraseology and terminology employed above are for the purpose of describing the disclosed embodiments and investigations, and do not necessarily serve as limitations to the scope of the invention. Therefore, the scope of the invention is to be limited only by the following claims.

The invention claimed is:

1. A process for preparing sorbose from glucose, the process comprising:
    contacting the glucose with a silica-containing structure comprising a zeolite having a topology of a 10-membered ring or smaller and Lewis acidic $M^{4+}$ framework centers wherein M is Ti, Sn, Zr, or Hf, wherein contacting the glucose is conducted under reaction conditions sufficient to isomerize the glucose to sorbose.

2. The process of claim 1, wherein the sorbose is L-(−)sorbose and the glucose is D-(+)-glucose.

3. The process of claim 2, wherein the silica-containing structure comprises Ti-CON (Ti-SSZ-33).

4. The process of claim 2, wherein the silica-containing structure consists of Ti-CON (Ti-SSZ-33).

5. The process of claim 2, wherein the silica-containing structure comprises Ti-MFI (TS-1).

6. The process of claim 2, wherein the silica-containing structure consists of Ti-MFI (TS-1).

7. The process of claim 2, wherein the silica-containing structure comprises nanosheet Ti-MFI (Ti-MFI-NS).

8. The process of claim 2, wherein the silica-containing structure consists of nanosheet Ti-MFI (Ti-MFI-NS).

9. The process of claim 1, wherein the silica-containing structure comprises Ti-CON (Ti-SSZ-33).

10. The process of claim 1, wherein the silica-containing structure consists of Ti-CON (Ti-SSZ-33).

11. The process of claim 1, wherein the silica-containing structure comprises Ti-MFI (TS-1).

12. The process of claim 1, wherein the silica-containing structure consists of Ti-MFI (TS-1).

13. The process of claim 1, wherein the silica-containing structure comprises nanosheet Ti-MFI (Ti-MFI-NS).

14. The process of claim 1, wherein the silica-containing structure consists of nanosheet Ti-MFI (Ti-MFI-NS).

15. The process of claim 1, wherein the reaction conditions comprise reaction temperatures of 333K to 473K and durations of 0 to 86,400 seconds.

16. The process of claim 1, wherein the reaction conditions comprise reaction temperatures of 353K to 393K and durations of 1800 to 21,600 seconds.

17. The process of claim 1, wherein the reaction conditions comprise stirring the glucose and the silica-containing structure at an autogenous pressure.

* * * * *